United States Patent [19]
Heath et al.

[11] Patent Number: 5,605,460
[45] Date of Patent: Feb. 25, 1997

[54] ENDODONTIC INSTRUMENT AND PROCEDURE

[75] Inventors: Derek E. Heath; Jerry A. Mooneyhan, both of Johnson City, Tenn.

[73] Assignee: Tulsa Dental Products, L.L.C., Tulsa, Okla.

[21] Appl. No.: 427,806

[22] Filed: Apr. 26, 1995

[51] Int. Cl.⁶ ....................................................... A61C 5/02
[52] U.S. Cl. ............................................. 433/224; 433/102
[58] Field of Search .................................... 433/102, 164, 433/224, 141

[56] References Cited

U.S. PATENT DOCUMENTS

| | | | |
|---|---|---|---|
| 3,855,702 | 12/1974 | Malmin | 433/224 |
| 3,949,479 | 4/1976 | Malmin | 433/224 |
| 4,019,254 | 4/1977 | Malmin | 433/102 |
| 4,392,827 | 7/1983 | Martin | 433/224 |
| 4,934,934 | 6/1990 | Arpaio, Jr. et al. | 433/102 |
| 4,971,556 | 11/1990 | Ritano | 433/102 |
| 5,017,138 | 5/1991 | Schilder | 433/102 |
| 5,106,298 | 4/1992 | Heath et al. | 433/102 |
| 5,125,838 | 6/1992 | Seigneurin | 433/102 |
| 5,380,200 | 1/1995 | Heath et al. | 433/102 |

FOREIGN PATENT DOCUMENTS

| | | | |
|---|---|---|---|
| 0257961 | 3/1988 | European Pat. Off. | 433/102 |
| 2022475 | 12/1979 | United Kingdom | 433/102 |

OTHER PUBLICATIONS

"Endodontics" by John I. Ingle, 2d Ed., 1976, Chapter 4, pp. 223–307.

Primary Examiner—Nicholas D. Lucchesi
Attorney, Agent, or Firm—Bell, Seltzer, Park & Gibson, P.A.

[57] ABSTRACT

A kit of endodontic instruments for use in root canal therapy wherein each instrument comprises an elongate blade having a proximate end and an opposite distal end, and with the blades of the instruments in the kit respectively having progressively increasing tapers. The kit is employed to fill an extirpated root canal with gutta percha, and instruments of progressively increasing taper are used in sequence during the obturation procedure so as to control the compaction of the gutta percha points in the canal.

14 Claims, 3 Drawing Sheets

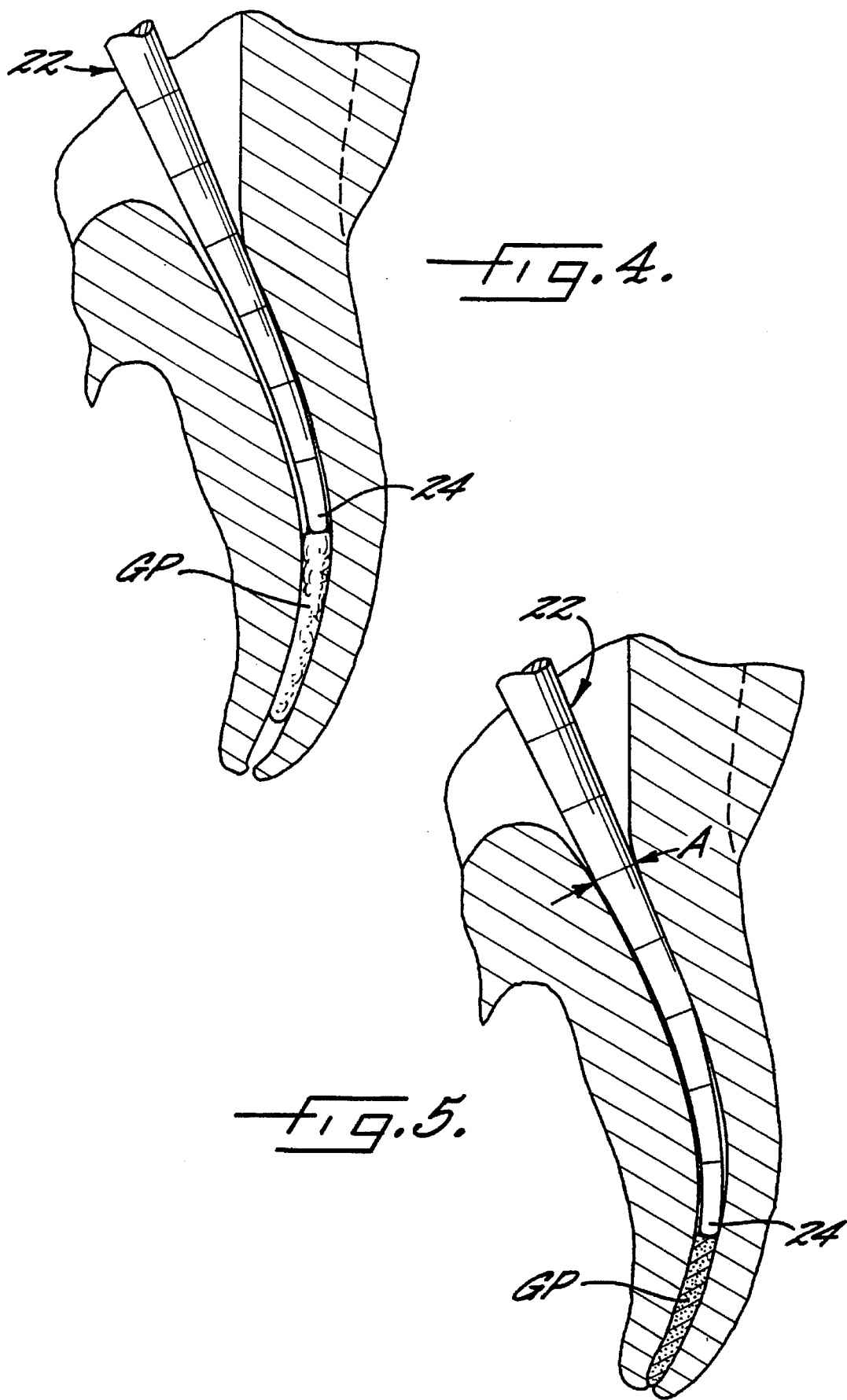

ENDODONTIC INSTRUMENT AND PROCEDURE

BACKGROUND OF THE INVENTION

The present invention relates generally to the field of endodontics, and more particularly to a method of applying a filler material in an endodontically prepared root canal.

Root canal therapy is a well-known procedure wherein the crown of a diseased tooth is opened so as to permit the canal to be cleaned and then filled. More particularly, after the crown is opened so as to expose the root canal, a series of very delicate, flexible, finger-held instruments or files are used to extirpate or clean out and shape the root canal, and each file is manually rotated and reciprocated in the canal by the dentist. Files of increasingly larger diameter are used in sequence, to achieve the desired cleaning and shaping. When the canal is thus prepared, it is obturated or filled with a filling material, which typically comprises a waxy, rubbery compound known as gutta percha.

In one traditional method of obturating a root canal, referred to as to as the warm gutta percha vertical compaction technique, strand-like pieces of warm gutta percha, commonly referred to as "points", are inserted into the extirpated root canal. The points are then physically compacted by a rod-like, blunt ended instrument called a plugger, which is inserted into the canal and manipulated into contact with the points to compact the material into the canal.

A set of rod-like pluggers of graduated diameters, but of uniform taper, may be employed during the compaction process. More particularly, at least one gutta percha point is initially inserted into the lower or apical third of the canal, and a plugger of small diameter is then employed to crush the point into the canal. Small additional pieces of warm gutta percha are then inserted, and the procedure is repeated using pluggers of increasing diameter, and so as to obturate the entire canal cavity.

As an alternative to using warm gutta percha points, it is also known to utilize cold gutta percha, which is heated in the canal by means of a heated spreader, which has a pointed end which is able to penetrate into the gutta percha and heat the material prior to being compacted by the plugger.

A potential problem associated with the either the warm or cold gutta percha vertical compaction technique is the risk that the forward end of a plugger, or the gutta percha, can be forced past the apex of the canal. Also, it is easier for the gutta percha to flow downwardly toward the apex, rather than laterally, and thus the complete filling of the canal in the lateral direction may not be achieved. It is also possible that the gutta percha can flow upwardly between the plugger and the wall of the canal, and flow out from the upper canal opening, rather than flowing downwardly and laterally to fill the canal.

A further problem associated with the known vertical compaction technique is the fact that a substantial portion of the crown of the tooth must be removed and widely flared in order to provide sufficient space for the pluggers and spreaders to get around the curves in the canal and reach substantially to the apex of the canal. This can severely weaken the crown of the tooth, and can result in the fracture and complete loss of the tooth.

It is accordingly an object of the present invention to provide a kit of obturating instruments, and a novel process utilizing such instruments, to perform a vertical compaction procedure, and which avoids the above noted problems and disadvantages of the prior art techniques.

SUMMARY OF THE INVENTION

The above and other objects and advantages of the present invention are achieved in the embodiment illustrated herein by the provision of a kit of endodontic obturating instruments, with each of the instruments comprising an elongate blade having a proximate end and an opposite distal end, and with the blades of the instruments respectively having progressively increasing tapers. The blade of each of the instruments preferably is of circular cross-sectional outline and has a smooth, non-fluted exterior surface, and the distal end of the blade of each instrument comprises a blunt transverse end surface. Also, the blade of each of the instruments preferably comprises an alloy of nickel and titanium so as to provide a high degree of flexibility and resistance to breakage and wear.

In accordance with the endodontic procedure of the present invention, the root canal is first extirpated or cleaned, by successively inserting a plurality of tapered files in the canal and manipulating each file in the canal. Files of progressively increasing diameter are employed, and so as to form the canal into a generally conical configuration which includes a relatively wide crown portion and an apex at the inner end of the canal. At least one gutta percha point is inserted into the extirpated root canal, and the distal end of the blade of a selected one of the kit of obturating instruments is then introduced into the root canal so as to engage and compact the gutta percha point toward the apex of the canal. The selected obturating instrument has a taper which is greater than the taper of the extirpated conical root canal, and so that the blade of the obturating instrument engages the crown portion of the root canal, and the distal end thereof is precluded from reaching the apex of the canal. The engagement of the blade with the crown portion of the canal closes the upper end of the canal and thus assures that the gutta percha flows downwardly toward the apex and not upwardly and out of the canal. Also, by selecting the taper of the plugger, the compaction of the gutta percha can be controlled in the apical region of the canal so as to not appreciably flow through the apex.

Typically, the endodontic procedure will include the further subsequent steps of inserting an additional gutta percha point into the extirpated root canal above the previously compacted point, and then inserting the distal end of the blade of a second obturating instrument from the kit and which has a taper greater than that of the blade of the previously inserted instrument. The blade of the second instrument thus engages and forces the additional gutta percha point toward the apex of the canal, and the blade of the second instrument engages the crown portion of the root canal and again closes the canal so that the distal end of the blade of the instrument is precluded from reaching into the canal to the extent reached by the blade of the first mentioned obturating instrument. Thus the compaction of the additional gutta percha can be controlled by selecting the taper of the second instrument.

Preferably, the blade of each of the obturating instruments, and the shank of each of the files is composed of an alloy comprising at least about 40% titanium and at least about 50% nickel. This composition provides a high degree of flexibility, and thus permits the instruments to pass around the curves in the canal, even in the case of severely curved canals, without requiring the removal and wide flaring of the crown portion of the canal. Thus, the procedure may be performed without unduly weakening the crown of the tooth. The use of a nickel-titanium alloy also reduces the risk of breakage and wear, as compared to conventional stainless steel materials.

BRIEF DESCRIPTION OF THE DRAWINGS

Some of the objects and advantages of the present invention having been stated, others will appear as the description proceeds, when taken in conjunction with the accompanying drawings, in which

FIGS. 4–7 are views of the sequential steps involved in obturating a root canal in accordance with the present invention.

DETAILED DESCRIPTION OF THE PREFERRED EMBODIMENT

Figure 1:
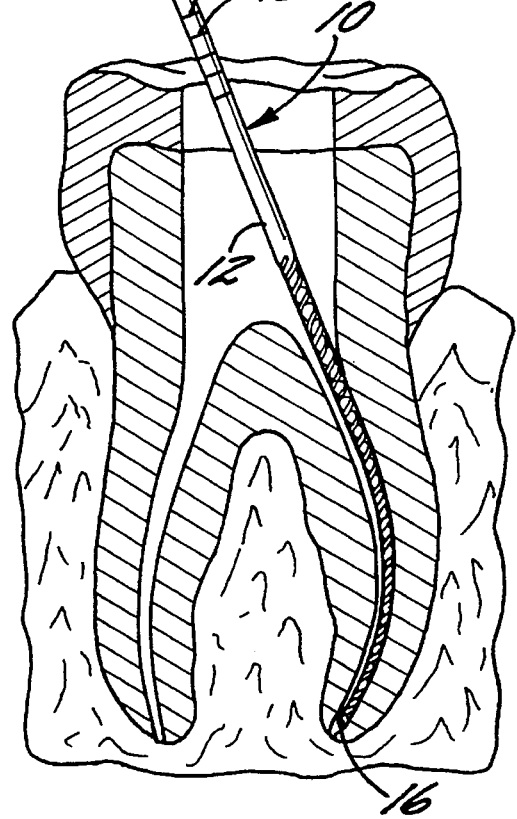
FIG. 1 is a sectional side elevation view of a tooth undergoing root canal therapy, in accordance with the present invention.

In performing root canal therapy, the crown of the tooth is initially opened, and the root canal is extirpated or cleaned. As illustrated in FIG. 1, the extirpation is conducted by successively inserting a plurality of tapered files 10 in the canal, and manipulating each file by simultaneous rotation and axial reciprocation. Files of progressively increasing diameter are used in sequence, and so as to form the canal into a general conical (albeit curved) configuration, and including a relatively wide crown portion and an apex at the inner end of the root canal.

Endodontic files of the described type are commonly supplied to the clinician in kits which comprise several files of increasing diameter. In particular, and in accordance with ANSI/ADA Specification No. 28-1988, files are provided in diameters which range from 0.08 mm at the tip (size 08) to 1.40 mm at the tip (size 140), and the files are provided in kits which contain a number of files of increasing diameter so that the files from a particular kit may be used in sequence by the clinician in accordance with the requirements of the particular canal being cleaned.

Each file 10 comprises a metallic shank 12, which typically has a length of about 30 mm, and a conventional handle 14 is mounted at the proximate end of the shank for engagement between the thumb and forefinger of the dentist during the manipulation thereof.

The portion of the shank 12 immediately below the handle 14 is cylindrical and has a diameter of between about 0.5 and 1.6 mm, and this shank portion includes calibrated depth markings 15 of conventional design. The shank further includes an opposite distal or pilot end, and a working length which is defined adjacent the pilot end. The working length is preferably slightly tapered toward the pilot end at an included angle of between about ½° and 4°.

The working length of the illustrated embodiment of the file 10 further comprises two continuous helical flutes which extend along its length. The flutes are preferably machined in the outer surface of the file in the manner further described in U.S. Pat. Nos. 4,934,934, and 5,380,200. This machining operation may result in the two flutes having a curved concave wall when viewed in transverse cross-section, and a helical land which is positioned between axially adjacent flute sections. Alternatively, a machining operation may be employed which produces a triangular or quadrangular cross-section (not shown). The configuration and structure of the preferred embodiment of the file is further described in the two above-referenced patents and in U.S. Pat. No. 5,106,298, the disclosures of which are expressly incorporated herein by reference.

Preferably, the shank 12 of the file 10 is composed of a nickel-titanium alloy which provides increased flexibility and wear resistance, and better resistance to breakage, as compared to the more conventional stainless steel composition. For example, the alloy may comprise at least about 40% titanium and at least about 50% nickel, and as a specific preferred example, "55-Nitinol" alloy may be used for the shank and which contains 54 to 56 weight percent nickel with the balance comprising titanium.

Figure 2:
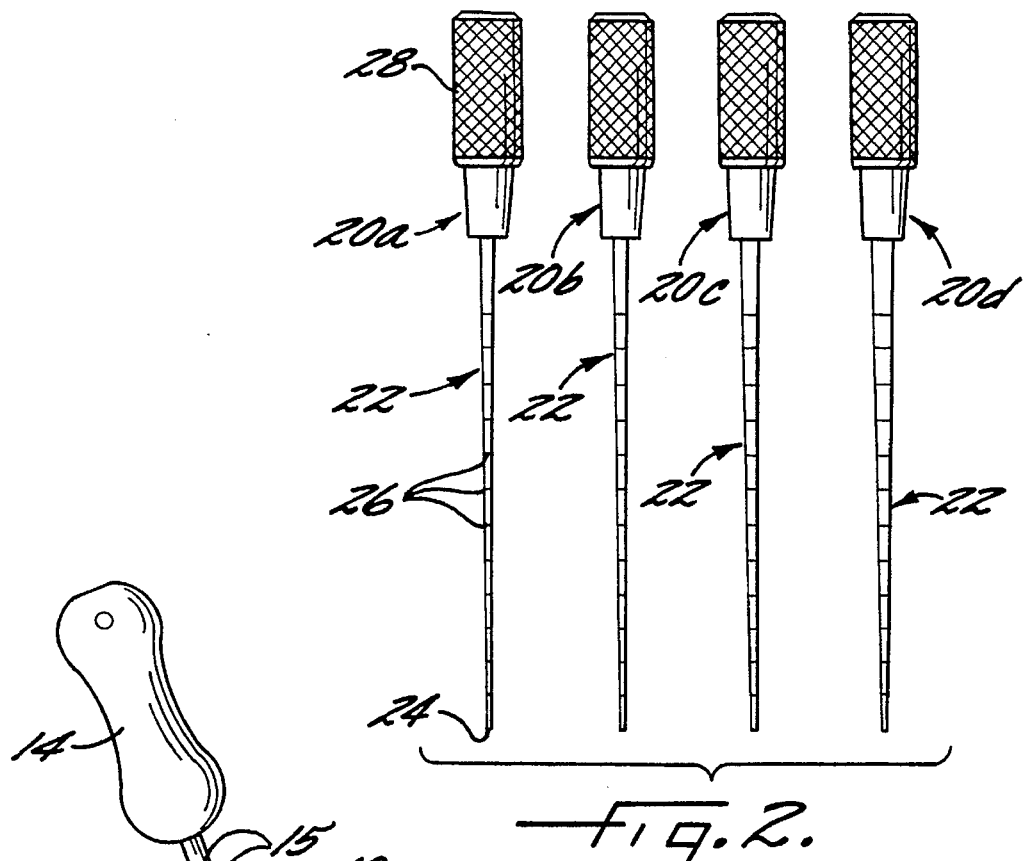
FIG. 2 is a side elevational view of a kit of obturating instruments in accordance with the present invention.

After the extirpation step is completed, the obturation process is commenced, which utilizes a kit of obturating instruments 20a, 20b, 20c, 20d as illustrated in FIG. 2. More particularly, each of the obturating instruments, which are commonly called pluggers, comprises an elongate rod-like blade 22 having a proximate end 23 and an opposite distal end 24. The blade 22 of each of the instruments is of circular cross-sectional outline and has a smooth, non-fluted exterior surface. Also, the blades of the instruments are tapered from the proximate end toward the distal end, with the blades of the instruments in the kit respectively having progressively increasing tapers. For example, the blade of each instrument in the kit is tapered at an included angle of between about ½° and 5°, and as a specific example, the blade of the instrument 20a of the kit may have a taper with an included angle of about 1°, the second instrument 20b may have a taper of about 2°, the third instrument 20c may have a taper of about 3°, and the fourth instrument 20d may have a taper of about 4°. Also, the distal end 24 of the blade of each of the instruments comprises a blunt transverse end surface.

Preferably, the blade 22 of each of the instruments comprises an alloy of nickel and titanium, so as to provide improved flexibility, wear resistance, and resistance to breakage, as compared to the conventional stainless steel composition. Preferably, the alloy comprises at least about 40% titanium and at least about 50% nickel, and most preferably "55-Nitinol" alloy as described above is employed.

The blade 22 of each of the instruments also preferably includes a plurality of axially spaced apart depth calibration markings 26 along its length, at for example 5 mm intervals, as is conventional. Also, a handle 28 is mounted at the proximate end of the blade of each of the instruments.

Figure 3:
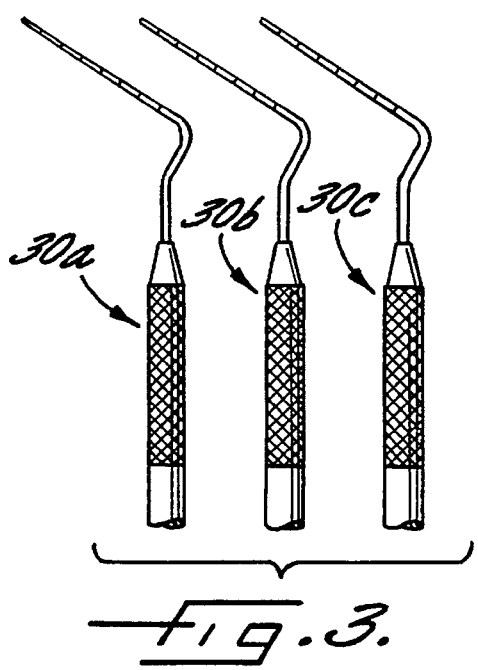
FIG. 3 is a side elevational view of a second embodiment of a kit of obturating instruments in accordance with the present invention.

The instruments 20a–20d illustrated in FIG. 2 are commonly referred to as "finger" pluggers, since the handles 28 are configured to be engaged between the thumb and forefinger of the dentist during use. FIG. 3 illustrates another kit of obturating instruments 30a, 30b, 30c in accordance with the present invention, and which are commonly referred to as "hand" pluggers since the handles are sized and configured to be engaged by the hand of the dentist in the manner of a pencil. The blades of the instruments shown in FIG. 3 respectively have progressively increasing tapers in the manner of the instruments shown in FIG. 2. Also, the blades of the instruments shown in FIG. 3 have an arcuate medial portion and a straight distal end portion, so as to permit the handles to be comfortably held in the hand of the dentist.

As illustrated in FIGS. 4–7, the obturation process is initiated by inserting one or perhaps two gutta percha points GP into the extirpated root canal, with the points being sized so that they fall into the apical third of the canal. One of the obturating instruments is then selected, with the selected instrument having a taper slightly greater than that of the last file used in the extirpation of the canal, and the distal end 24 of the blade 22 of the selected instrument is then inserted into the canal, so that the blunt end surface of the blade engages the gutta percha. An axial force is then applied to the instrument, so as to force the gutta percha toward the apex of the canal. Since, the selected obturating instrument has a taper which is greater than the taper of the extirpated conical root canal, the blade 22 engages the crown portion of the root canal as indicated at A in FIG. 5 when the blade is inserted a predetermined distance, and such that the distal end 24 is precluded from reaching the apex of the canal. The engagement at the point A also closes the upper end of the canal and thus assures that the gutta percha flows downwardly toward the apex and not upwardly and out of the canal. Also, the gutta percha is forced laterally, so as to provide for the complete filling of the canal in the lateral direction.

Figure 6:
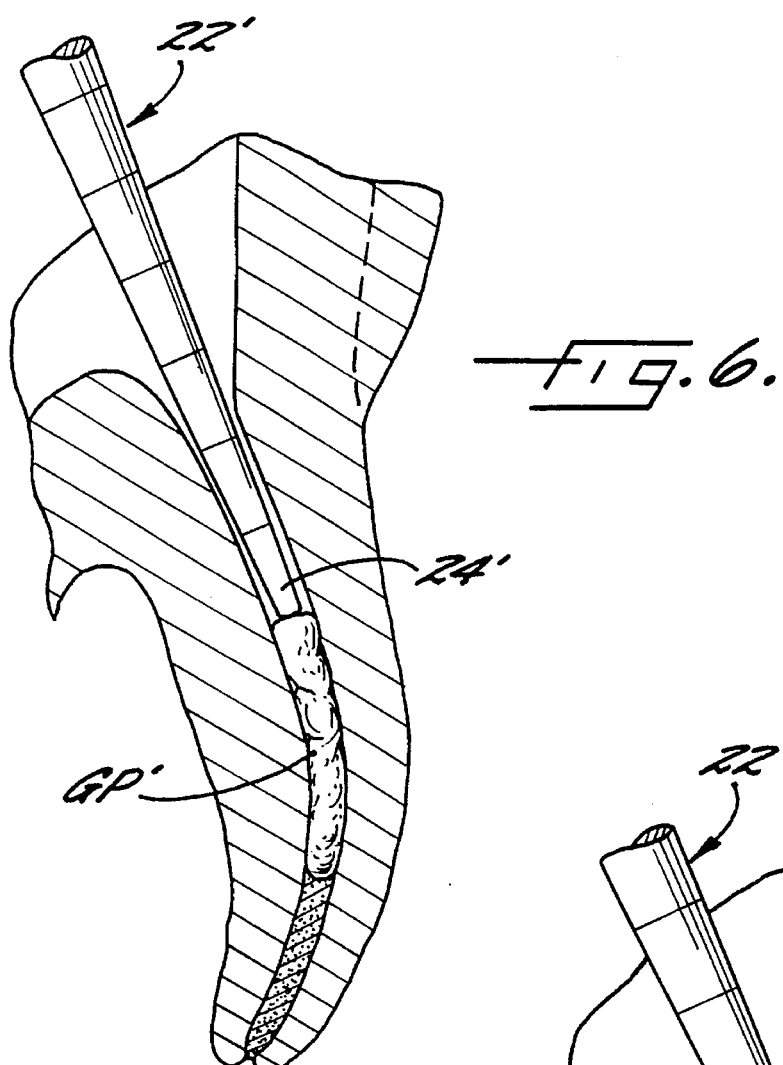
Figure 7:
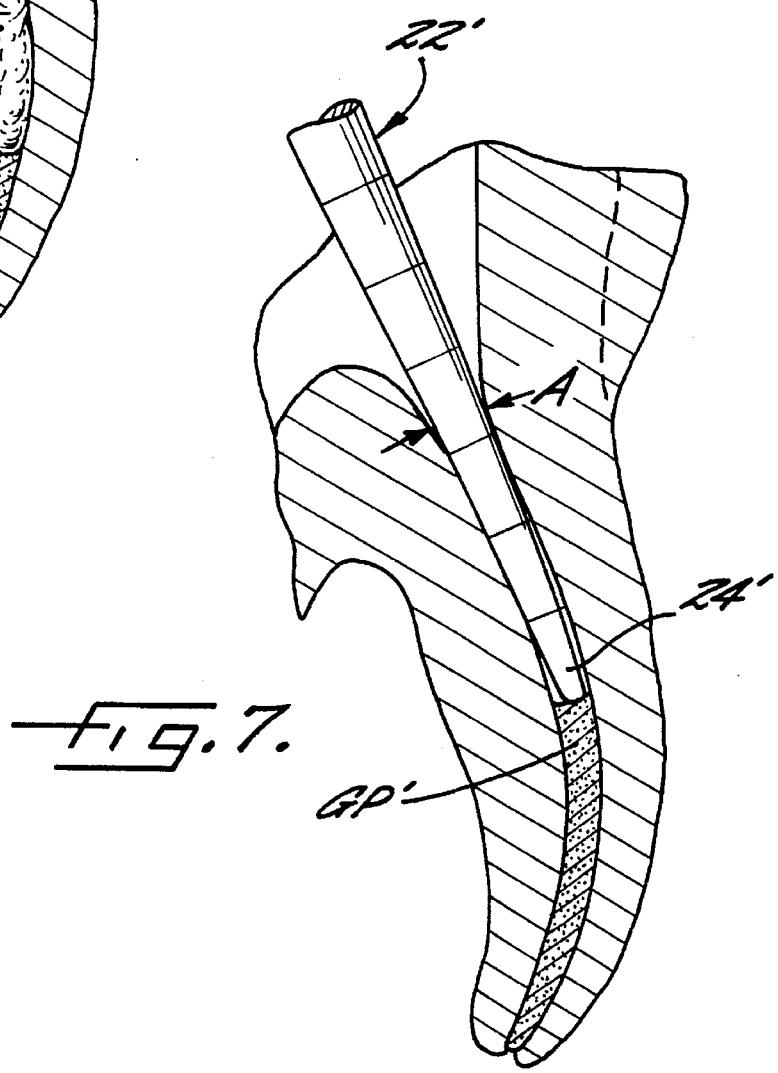

The instrument is then withdrawn, and one or more additional points of gutta percha are inserted into the canal as illustrated at GP' in FIG. 6. The distal end of the blade 22' of a second obturating instrument, which has a taper greater than that of the first instrument, is inserted into the root canal so as to engage and force the additional gutta percha points GP' toward the apex of the canal. Here again, the second instrument is selected so as to have a taper wherein the blade engages the crown portion at the point A as seen in FIG. 7, with the distal end 24' thereof being thereby precluded from reaching into the canal to the extent reached by the blade of the first instrument. Thus, the proper degree of axial and lateral compaction of the additional points may be assured, again without flow out of the canal in the upward direction.

The above steps of inserting additional points and compacting the points with instruments of increasing taper is repeated until the canal is completely filled with the gutta percha. The crown is then closed in the conventional manner, so as to complete the root canal procedure.

In the drawings and specification, there have been set forth preferred embodiments of the invention, and although specific terms are employed, they are used in a generic and descriptive sense only and not for purposes of limitation.

That which is claimed:

1. A kit comprising a plurality of endodontic obturating instruments which are adapted for use in performing root canal therapy, with each of the instruments comprising an elongate blade having a proximate end and an opposite distal end, with the blade of each of said instruments having circular cross-sectional outline and a smooth, non-fluted exterior surface, and with the blades of said instruments respectively having progressively increasing tapers.

2. The kit as defined in claim 1 wherein the distal end of the blade of each of said instruments comprises a blunt transverse end surface.

3. The kit as defined in claim 2 wherein the blade of each of said instruments comprises an alloy comprising nickel and titanium.

4. The kit as defined in claim 3 wherein the blade of each of said instruments comprises an alloy comprising at least about 40% titanium and at least about 50% nickel.

5. The kit as defined in claim 1 wherein the blade of each of said instruments includes a plurality of axially spaced apart depth calibration markings.

6. The kit as defined in claim 1 wherein the blade of each of said instruments is tapered at an included angle of between about ½ and about 5 degrees.

7. The kit as defined in claim 1 wherein each of said instruments further comprises a handle mounted at said proximate end of the associated blade.

8. An endodontic procedure comprising the steps of extirpating a root canal and including successively inserting a plurality of tapered files in the canal and manipulating each file in the canal, with the files being of progressively increasing diameter, and so as to form the canal into a general conical configuration including a relatively wide crown portion and an apex at the inner end of the root canal, providing a kit of endodontic obturating instruments, with each of the instruments comprising an elongate blade having a proximate end and an opposite distal end, and with the shanks of the instruments respectively having progressively increasing tapers, inserting at least one gutta percha point into the extirpated root canal, inserting the distal end of the blade of a selected one of the obturating instruments into the root canal so as to engage and force the one gutta percha point toward the apex of the canal, and with the selected obturating instrument having a taper which is greater than the taper of the extirpated conical root canal and so that the blade of the obturating instrument engages the crown portion of the root canal and the distal end of the blade is precluded from reaching the apex of the canal.

9. The endodontic procedure as defined in claim 8 comprising the further subsequent steps of inserting at least one additional gutta percha point into the extirpated root canal above the previously inserted point, and then inserting the distal end of the blade portion of a second obturating instrument having a taper greater than that of the blade of the previously inserted instrument into the root canal so as to engage and force the additional gutta percha point toward the apex of the canal, and so that the blade of the second obturating instrument engages the crown portion of the root canal and the distal end thereof is precluded from reaching into the canal to the extent reached by the blade of the first mentioned obturating instrument.

10. The endodontic procedure as defined in claim 9 wherein the blade of each of said obturating instruments is of circular cross-sectional outline and defines a blunt transverse end surface.

11. The endodontic procedure as defined in claim 10 wherein the blade of each of said obturating instruments comprises an alloy comprising at least about 40% titanium and at least about 50% nickel.

12. The endodontic procedure as defined in claim 10 wherein each of said plurality of files comprises an elongate shank having a proximate end and an opposite pilot end, and so as to define a working length adjacent said pilot end, and at least one continuous helical flute formed so as to extend along the length of said working length, with each of said flutes defining a cutting edge along each side edge thereof.

13. The endodontic procedure as defined in claim 12 wherein the shank of each of said files includes a helical land positioned between axially adjacent flute segments.

14. The endodontic procedure as defined in claim 13 wherein the blade of each said obturating instruments and the shank of each of said files is composed of an alloy comprising at least about 40% titanium and at least about 50% nickel.

* * * * *